United States Patent [19]

Doutre

[11] Patent Number: 4,926,114
[45] Date of Patent: May 15, 1990

[54] APPARATUS FOR STUDYING PARTICLES HAVING AN APERTURE WHOSE CROSS-SECTIONAL AREA CHANGES PROGRESSIVELY ALONG AT LEAST PART OF ITS LENGTH

[75] Inventor: Don A. Doutre, Jonquiere, Canada

[73] Assignee: Alcan International Limited, Montreal, Canada

[21] Appl. No.: 405,042

[22] Filed: Sep. 8, 1989

Related U.S. Application Data

[63] Continuation of Ser. No. 833,059, Feb. 24, 1986, abandoned.

[30] Foreign Application Priority Data

Feb. 27, 1985 [GB] United Kingdom ............... 8505047

[51] Int. Cl.⁵ .................................... G01N 27/02
[52] U.S. Cl. ................................ 324/71.4; 324/71.1
[58] Field of Search .............. 324/71.1, 71.4; 377/11, 377/12

[56] References Cited

U.S. PATENT DOCUMENTS

| | | | |
|---|---|---|---|
| 2,434,835 | 1/1948 | Colley | 324/71.4 X |
| 2,998,198 | 8/1961 | Young | 324/71.4 X |
| 3,390,326 | 6/1968 | Imadate | 324/71.4 X |
| 3,441,848 | 4/1969 | Valley et al. | 324/71.1 |
| 3,628,140 | 12/1971 | Hogg et al. | 324/71.1 |
| 3,924,180 | 12/1975 | Salzman et al. | 324/71.1 |
| 4,491,786 | 1/1985 | Godin | 324/71.4 X |
| 4,555,662 | 11/1985 | Doutre et al. | 324/71.4 |

Primary Examiner—Reinhard J. Eisenzopf
Assistant Examiner—Jack B. Harvey
Attorney, Agent, or Firm—Cooper & Dunham

[57] ABSTRACT

Apparatus and method for studying particles suspended in an electrically conducting fluid by providing an aperture with a current path therethrough, causing the fluid to flow through the aperture and detecting resistive pulses caused by the passage of suspended particles. Additional information about particle size is generated by designing the aperture such that its cross-section changes progressively along its length, and observing the duration of the resistive pulses, which duration varies with particle size. The method is particularly useful for the study of particles suspended in molten metal.

5 Claims, 3 Drawing Sheets

APPARATUS FOR STUDYING PARTICLES HAVING AN APERTURE WHOSE CROSS-SECTIONAL AREA CHANGES PROGRESSIVELY ALONG AT LEAST PART OF ITS LENGTH

This is a continuation of application Ser. No. 833,059, filed Feb. 24, 1986, now abandoned.

U.S. Pat. No. 2,656,508 issued 20th Oct., 1953 describes a system, known as the resistive pulse technique, for counting particles suspended in an electrically conducting fluid medium. An electrically insulating wall, including an aperture several to several hundred microns in diameter, is immersed in the fluid. A pair of electrodes are disposed in the fluid on opposite sides of the wall to establish a current path between them through the fluid and passing through the aperture. The fluid is caused to pass through the aperture at a known rate, and an electric current is passed between the two electrodes. The aperture and the resulting constricted electric field in and around it constitute a scanning zone.

While pure fluid is passing through the aperture, the resistance between the two electrodes, and in consequence also the voltage, is steady. When a particle suspended in the fluid passes through the aperture (or, more accurately, through the scanning zone), the resistance is altered, being increased if the electrical conductivity of the particle is lower than that of the fluid as is generally the case. Under constant current conditions, the passage of a suspended particle through the aperture gives rise to a voltage pulse which is readily detected. Alternatively, given constant voltage conditions, the passage of a suspended particle gives rise to a current pulse, in this case a transient reduction in current. Knowing the rate of fluid flow and the rate of occurrence of voltage pulses it is easily possible to calculate the number of particles per unit volume of fluid. Since 1953, the system has been greatly developed and refined and a large volume of patents and literature now exists in respect of it.

Various patents including U.S. No. 3,668,531 describe how it is possible to use the amplitude of each voltage pulse to determine the size of the particle responsible. U.S. Pat. No. 3628140 provides a conical chamber upstream and/or downstream of the aperture in order to increase resolution.

U.S. Pat. No. 3,441,848 is concerned with measuring the lengths of fibres. Fibres suspended in a fluid pass through an aperture lengthwise, and the patent takes advantage of this to use the duration of each voltage pulse to determine the length of the fibre responsible. In U.S. No. 3,890,568, a combination of voltage pulse amplitude and duration are used to provide a more accurate measure of fibre length.

The system thus far described has been essentially concerned with aqueous fluids, having ionic conductivity characteristics. By European Patent Specification 119770 the concept has been extended to molten metals, having electronic conductivity characteristics, for which purpose a high current density is required.

In all these systems, the cross-sectional area of the aperture has been constant along its length, or has been shaped at its upstream and downstream ends to achieve non-turbulent flow of fluid, but has not been caused to change along its length in any systematic way in order to provide additional information.

According to the present invention, the aperture has a finite length in the direction of flow of the fluid and the cross-section of the aperture is caused to change progressively along at least part of its length. As a result of this progressive change in cross-section, the duration of a resistive pulse caused by passage of a particle through the aperture depends on the size of the particle. According to the invention, the duration of resistive pulses is analysed and provides information about the particle size. By resistive pulse is meant either a transient increase in voltage at constant current or a transient decrease in current at constant voltage. In the preferred mode of practicing the invention, constant current conditions are used, and the length of time the voltage exceeds an arbitrary threshold value is measured.

The progressive change in cross-section can be achieved by providing a truncated cone-shaped aperture. Alternatively the aperture can be shaped like the hole in a torus. Other shapes are possible.

Figure 1:
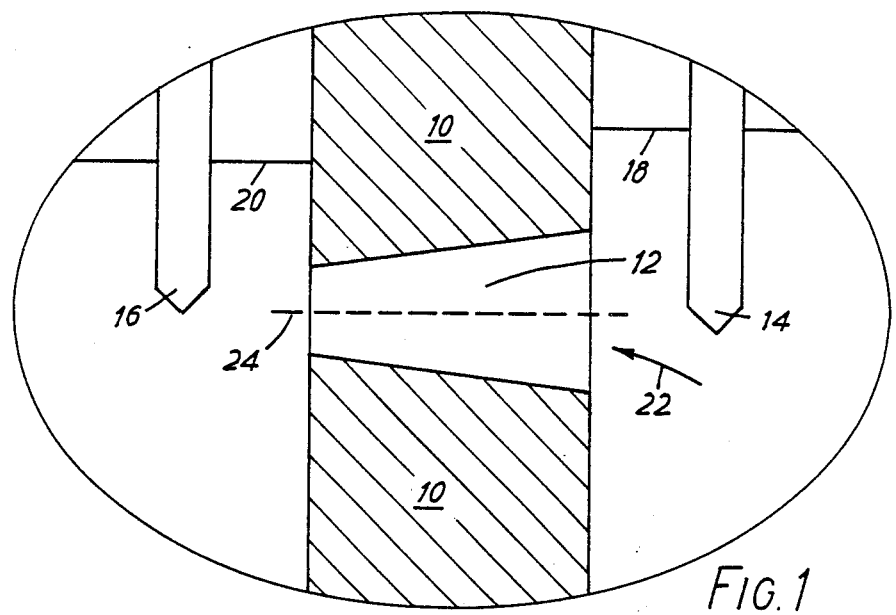
FIG. 1 is a schematic diagram of apparatus according to the invention.

Referring to FIG. 1, there is provided an electrically insulating wall 10 including an aperture 12 therethrough, a pair of electrodes 14, 16 disposed on opposite sides of the wall, all immersed in an electrically conducting fluid having surfaces 18, 20 on opposite sides of the wall. The fluid is caused to pass through the aperture in the direction of the arrow 22 at a controlled flow rate. A constant current is passed between the electrodes, and voltage pulses caused by particles passing through the aperture are detected and analysed (by means not shown).

The aperture is shown as having the shape of a truncated cone having a longitudinal axis 24 and a diameter that decreases in the direction of flow of the fluid.

It can be shown (Deblois R. W. and Bean C. P. "Counting and Sizing of Sub-Micron Particles by the Resistive Pulse Technique." *Rev. Sci Instr.* Vol. 41 No. 7 Pp 909–915, 1970) that, when a substantially non-conducting particle passes through an opening of circular cross-sectional area (substantially larger than the cross-section of the particle), the resistance measured across the opening will be given by the following equation:

$$\Delta R = \left(\frac{\Delta V}{I}\right) = \frac{4\rho}{\pi} \cdot \frac{d^3}{D^4} \tag{1}$$

Where $\Delta R$: is the change in the electrical resistance of the opening $\Delta V$: is the corresponding change in voltage manifested in the presence of a current I $\rho$: is the resistivity of the fluid d: is the equivalent spherical diameter of the particle and D: is the diameter of the opening.

By re-arranging equation 1 one obtains $$D = \left[ \frac{4\rho}{\pi} \left( \frac{I}{\Delta V} \right) d^3 \right]^{\frac{1}{3}} = \left[ \frac{4\rho}{\pi} \cdot \frac{d^3}{\Delta R} \right]^{\frac{1}{3}} \quad (2)$$

which is an explicit expression for the opening diameter "D" at which a particle of diameter "d" will cause a change in the resistance of the opening of magnitude $$\Delta R. \left( \frac{\Delta V}{I} \right)$$

By examining FIG. 1 and equation (2), it is readily apparent that a larger particle will cause the resistance to change by an amount of ΔR earlier in its passage through the opening than will a smaller particle. Furthermore, as will be shown next, if the geometry of the opening is known and the flow conditions are appropriately chosen it is possible to establish a functional relationship between the duration over which the passage of a particle causes a minimum change in resistance and the dimension of the particle.

The case of an opening having the shape of a truncated cone serves as a convenient example.

Figure 2:
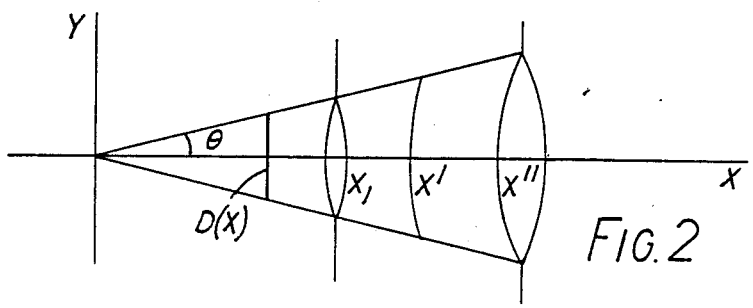
FIG. 2 represents a cone.

Consider the case of a particle of diameter "d" which gives rise to a change in resistance (ΔV/I) at some point "X" within the shaded portion of the cone shown in FIG. 2.

Fixing the origin at the apex of the cone, the base diameter "D" is simply:

$$D(X) = KX \quad (3)$$

where K is twice the tangent of the ½ angle (θ) subtended by the cone i.e. $D(X) = 2(\tan \theta) X$ \quad (4)

The volume of a cone is known to be:

$$\text{Vol} = \frac{1}{3} \pi \left( \frac{D}{2} \right)^2 h \quad (5)$$

where
h: the altitude of the cone
D: base diameter

Thus the volume of the truncated cone shown in FIG. 2 extending from $X_1$ to some distance X is:

$$V(X) = \frac{\pi}{3} \cdot X \left( \frac{D(X)}{2} \right)^2 - \frac{\pi}{3} \cdot X_1 \left( \frac{D(X_1)}{2} \right)^2 \quad (6)$$

substituting for $D(X) = \tan \theta (X)$ gives $$V(X) = \frac{\pi}{3} \cdot \tan^2 \theta \cdot (X^3 - X_1^3) \quad (7)$$

One may assume that there are no substantial velocity gradients within the fluid passing through the truncated cone. This is justified based on the observation that the volumetric flow rate through a small, thin opening can be predicted accurately by Bernoulli's Equation when the assumption of inviscid flow is made. With this assumption, the time "T" that it takes for the particle to pass from point X to point $X_1$ will be simply $$T = \frac{V(X)}{Q} \quad (8)$$

where Q is the volumetric flow rate of the liquid

Substituting equation (2) into equation (4) into equation (8) provides an explicit relationship between the Time over which a particle of diameter "d" will cause an increase in the electrical resistance ΔR of the opening of the particle diameter "d":

$$T = \frac{\pi}{3} \cdot \frac{\tan^2 \theta}{Q} \cdot \left( \left[ \frac{1}{2\tan \theta} \left( \frac{4\rho}{\pi} \cdot \frac{d^3}{\Delta R} \right)^{\frac{1}{3}} \right]^3 - X_1^3 \right) \quad (9)$$

or, more conveniently as in the preferred embodiment, in terms of the voltage change (ΔV) in the presence of an applied current I:

$$T = \frac{\pi}{24 \cdot \tan \theta \cdot Q} \left[ \left( \frac{4\rho \cdot I \cdot d^3}{\pi \cdot \Delta V} \right)^{\frac{1}{3}} - D_i^3 \right] \quad (10)$$

where Di is the diameter of the smaller end of the truncated cone.

As an example consider the case of molten aluminium ($Y = 25 \times 10^{-8} \Omega M$) being drawn through a truncated conical opening of inferior diameter $D_i = 3 \times 10^{-4}$ M and taper angle $\theta = 8.53$ degrees, at the rate of $2.67 \times 10^{-7}$ M³/sec (16 cc/min) in the presence of an applied current (I) of 60 amperes. The time T during which the threshold voltage (ΔV, in this case 10 μV) is exceeded during the passage of a particle of diameter (d) can be obtained by substitution into equation 10:

| d($10^{-6}$m) | T($10^{-6}$s) |
|---|---|
| 20 | 54 |
| 25 | 146 |
| 30 | 265 |
| 35 | 412 |
| 40 | 589 |
| 45 | 792 |
| 50 | 1030 |

The length of the aperture, in the direction of flow of the fluid, should be substantially greater than the length of individual particles, but sufficiently small that the aperture (or the sensing zone associated with it) generally contains not more than one particle at a time. With acicular particles such as fibres, the above equations apply only with somewhat less accuracy, and the invention is thus particularly useful where the suspended particles, as is generally the case with particles suspended in molten metals, do not differ markedly from spherical. The minimum diameter and angle of taper may be chosen having regard to the expected size range of the suspended particles. The upstream and downstream ends of the aperture may be profiled to promote streamlined fluid flow.

Figure 3:
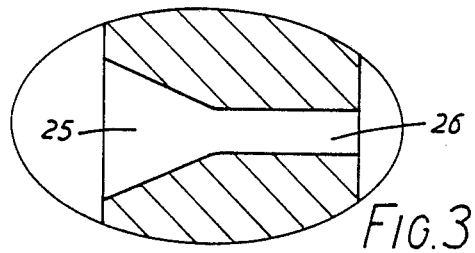
FIGS. 3 to 6 are axial sections through alternative apertures for use in the equipment of FIG. 1.

It is known that the amplitude of a voltage pulse generated by a particle passing through an aperture of constant cross-section can be analysed to provide a measure of particle size, and this technique can be used in conjunction with an aperture of the type shown in FIG. 3. In this Figure, an aperture has an upstream section 25 in the form of a truncated cone whose diameter decreases in the direction of the fluid flow (from left to right), and a downstream section 26 in the form of a cylinder. A measurement of the duration of a voltage pulse (above a datum level), as a particle passes through section 24 of the aperture, can be combined with a measurement of the amplitude of the voltage pulse, as the particle passes through section 26, to provide a good determination of particle size.

The aperture of FIG. 3 could alternatively be used with fluid flow from right to left, albeit with somewhat greater risk of turbulence.

Figure 4:
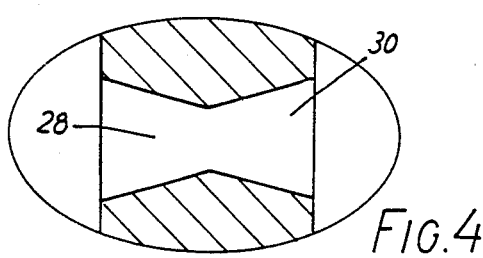

In FIG. 4, an aperture comprises an upstream section 28 in the form of a truncated cone of decreasing diameter, and a downstream section 30 in the form of a truncated cone of increasing diameter. This profile has the advantage that the change in duration of the voltage pulse for a given change in particle size is doubled in comparison with the profile of FIG. 1.

Figure 5:
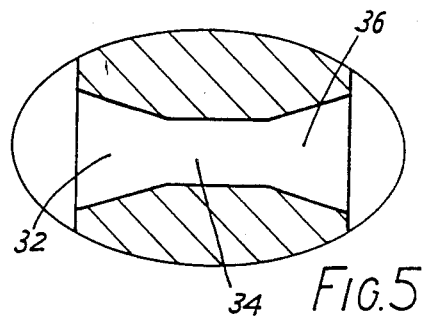

In FIG. 5, an aperture has an upstream section 32 in the form of a truncated cone of decreasing diameter, in intermediate section 34 in the form of a cylinder, and a downstream section 36 in the form of a truncated cone of increasing diameter.

Figure 6:
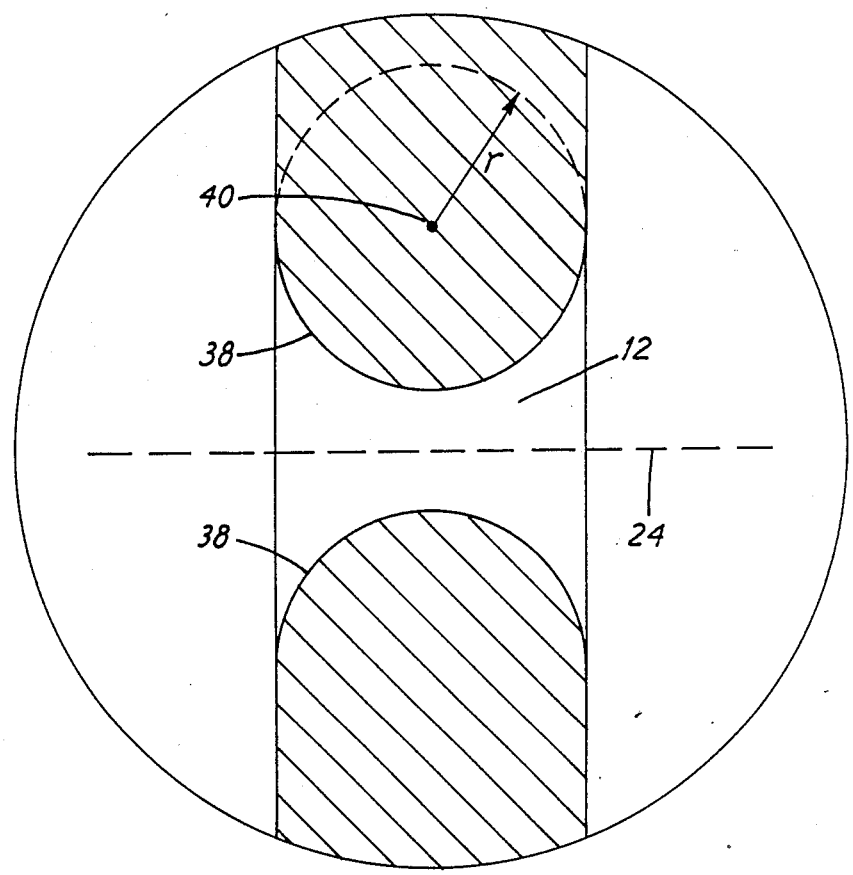

In FIG. 6, a wall 10 has an aperture 12 having a longitudinal axis 24. But the walls 38 defining the aperture are not straight in a direction parallel to the axis, but are curved. In fact the aperture has the shape of the hole in a torus and may be notionally generated by rotating a circle having a radius r centered at 40 round the axis 24. Alternatively, for the notional circle could have been substituted an ellipse with its major axis parallel or perpendicular to the axis 24 of the aperture. In fact the curved surfaces 38 could have been shaped in a variety of ways consistent with the requirement that the cross-sectional area of the aperture changes progressively along at least part of its length.

Figure 7:
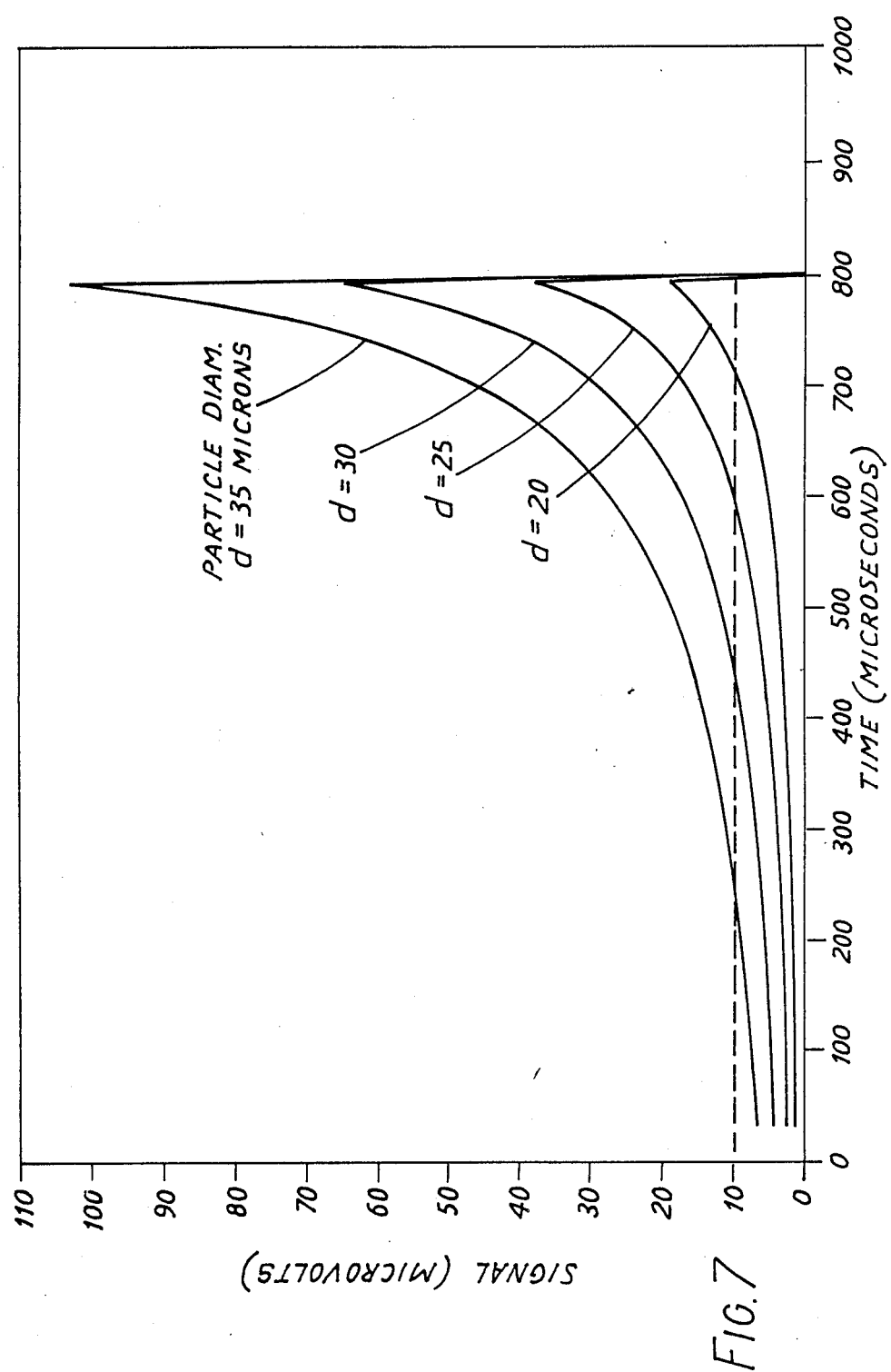
FIG. 7 is a graph of signal against time showing the profile of voltage pulses at different particle sizes.

FIG. 7 is a graphical presentation of the mathematical treatment of the invention. The graph is in the form of theoretical voltage-time curves for the passage of particles of diameters ranging from 20 to 35 microns through a conical aperture having a maximum diameter of 0.6 mm, a minimum diameter of 0.3 mm and a length of 1.3 mm. The curves have been generated by a computer programme using increments of distance, i.e. V has been calculated using equation (1) under constant current conditions, at increments of 5 microns measured along the axis of the aperture. A dashed line has been drawn to illustrate the fact that the duration for which the voltage pulse exceeds a given threshold value, say 10 microvolts, increases with increasing particle size.

EXAMPLE

An experiment was performed using equipment including a conical aperture as in FIG. 1 with dispersion of glass beads of known diameter in 1% w/w KCl solution in water. The following table sets out the durations of voltage pulses (in milliseconds above an arbitrary reference voltage) against the diameters of the beads.

| Voltage Pulse Duration (ms) | Bead Diameter (microns) |
| --- | --- |
| 0.18 | 57 |
| 0.48 | 85 |
| 0.60 | 107 |
| 0.64 | 103 |
| 0.59 | 103 |
| 0.18 | 56.8 |
| 0.20 | 56.8 |

The first three results were obtained using mixed beads in a single dispersion. It is apparent that the voltage pulse durations can be used to determine the bead diameters.

I claim:

1. Apparatus for studying substantially spherical particles suspended in an electrically conducting fluid comprising an electrically insulating wall including an aperture therethrough, a pair of electrodes disposed on opposite sides of the wall to establish a current path between them through the fluid and passing through the aperture, means for causing the fluid to pass at a controlled rate through the aperture and for simultaneously passing an electric current between the two electrodes by means of the said current path, and means for detecting changes in electrical resistance (resistance pulses) across the wall resulting from particles suspended in the fluid passing through the aperture, characterized in that the aperture has a finite length in the direction of flow of the fluid, the cross-sectional area of the aperture changes progressively along at least part of its said length, and the detecting means includes means for analysing the duration of the resistive pulses resulting from passage of substantially spherical particles through said last-mentioned part of said aperture length to provide information about the particle size.

2. Apparatus as claimed in claim 1, adapted for use under constant current conditions, wherein the means for detecting transient voltage increases.

3. A method of studying substantially spherical particles suspended in an electrically conducting fluid comprising establishing a sensing region within the fluid, which sensing region has a longitudinal axis and a cross-section area, causing an electric current to flow along a current path extending longitudinally of the sensing region, causing the fluid to flow at a controlled rate in a longitudinal direction through the sensing region, and detecting changes in the electrical resistance (resistive pulses) of the fluid passing thorugh the sensing region resulting from the presence therein of said particles, characterized in that the sensing region has a finite length in a longitudinal direction, the cross-section area of the sensing region changes progressively along at least part of the said length, and in that detecting resistive voltage pulses includes analysing the duration of the said pulses resulting from passage of substantially spherical particles through said last-mentioned part of said aperture length to provide information about the particle size.

4. A method as claimed in claim 3, wherein the electrically conducting fluid is a molten metal.

5. A method as claimed in claim 3, wherein current is caused to flow under constant current conditions, and changes in electrical resistance are detected in the form of transient voltage increases.

* * * * *